(12) United States Patent
Mejia Nino et al.

(10) Patent No.: US 11,408,444 B2
(45) Date of Patent: Aug. 9, 2022

(54) HYDRAULIC DAMPER WITH VALVE BLOCK

(71) Applicant: Otto Bock Healthcare Products GmbH, Vienna (AT)

(72) Inventors: Juan Pablo Mejia Nino, Mödling (AT); Florian Grafl, Vienna (AT)

(73) Assignee: Otto Bock Healthcare Products GmbH, Vienna (AT)

( * ) Notice: Subject to any disclaimer, the term of this patent is extended or adjusted under 35 U.S.C. 154(b) by 0 days.

(21) Appl. No.: 15/733,508

(22) PCT Filed: Feb. 20, 2019

(86) PCT No.: PCT/EP2019/054223
§ 371 (c)(1),
(2) Date: Aug. 14, 2020

(87) PCT Pub. No.: WO2019/162331
PCT Pub. Date: Aug. 29, 2019

(65) Prior Publication Data
US 2020/0378408 A1 Dec. 3, 2020

(30) Foreign Application Priority Data
Feb. 21, 2018 (DE) ................. 10 2018 103 884.4

(51) Int. Cl.
*F15B 11/024* (2006.01)
(52) U.S. Cl.
CPC ..... *F15B 11/024* (2013.01); *F15B 2011/0246* (2013.01)

(58) Field of Classification Search
CPC ................. F15B 2011/0246; F15B 11/024
See application file for complete search history.

(56) References Cited

U.S. PATENT DOCUMENTS 3,568,707 A * 3/1971 Shore .................... F15B 11/024
137/115.08
2002/0074197 A1 6/2002 Preukschat et al.
(Continued)

FOREIGN PATENT DOCUMENTS

DE 20313999 U1 11/2003
DE 10344152 A1 4/2005
(Continued)

OTHER PUBLICATIONS

International Search Report for International Application No. PCT/EP2019/054223, dated May 15, 2019, 2 pages.
(Continued)

*Primary Examiner* — F Daniel Lopez
(74) *Attorney, Agent, or Firm* — Holland & Hart LLP

(57) ABSTRACT

A hydraulic actuator includes a housing and with a chamber, which is arranged or formed in the housing and in which a piston is mounted movably and divides the chamber into a flexion chamber and an extension chamber. A channel for hydraulic fluid leads from the flexion chamber and the extension chamber into the housing in order to produce a fluidic connection between the flexion chamber and the extension chamber. At least one valve is arranged in the fluidic connection. The channels lead from the housing to a valve block in which the at least one valve is arranged and is fluidically coupled to the channels, and the valve block is connected to the housing.

14 Claims, 5 Drawing Sheets

(56) References Cited

U.S. PATENT DOCUMENTS

2015/0217621 A1    8/2015   Yamashita
2015/0305895 A1   10/2015   Boiten et al.

FOREIGN PATENT DOCUMENTS

| | | |
|---|---|---|
| DE | 102008027474 A1 | 12/2009 |
| DE | 202013006583 U1 | 12/2014 |
| DE | 102015201528 A1 | 8/2015 |
| DE | 102014007641 A1 | 11/2015 |
| EP | 1215413 A2 | 6/2002 |
| EP | 2922505 B1 | 6/2017 |
| EP | 3208488 A1 | 8/2017 |
| FR | 24035 E | 2/1922 |
| RU | 40584 U1 | 9/2004 |

OTHER PUBLICATIONS

Russian Patent Office; English Translation of Official Action in RU 2020122881/14; dated Apr. 1, 2022; 9 pages.

\* cited by examiner

HYDRAULIC DAMPER WITH VALVE BLOCK

CROSS REFERENCE TO RELATED APPLICATIONS

This application is a U.S. National Entry and claims priority to PCT International Patent Application No. PCT/EP2019/054223, filed 20 Feb. 2019, and entitled "HYDRAULIC DAMPER WITH VALVE BLOCK", which claims priority to Germany Patent Application No. 102018103884.4 filed 21 Feb. 2018, the entire disclosures of which are incorporated herein by this reference.

TECHNICAL FIELD

The invention relates to a hydraulic actuator having a housing, a chamber which is arranged or formed in the housing and in which a piston is movably mounted and divides the chamber into a flexion chamber and an extension chamber, a channel for hydraulic fluid leads from each of the flexion chamber and the extension chamber into the housing in order to produce a fluidic connection between the flexion chamber and the extension chamber, wherein at least one valve is arranged in the fluidic connection.

BACKGROUND

Hydraulic actuators are used in particular in orthopedic devices such as orthoses, prostheses or wheelchairs. They can either be configured as passive actuators and act as pure dampers or stops; alternatively, active actuators are known which are coupled with an energy store or drive in order to allow a housing to be displaced relative to a piston rod or to a drive element. Hydraulic actuators can be configured as linear actuators or rotary actuators. Hydraulic actuators have a hydraulic chamber which is filled with a hydraulic fluid, in particular an oil. The chamber within a housing is divided by a piston into an extension chamber and a flexion chamber, the volume of which can be changed. If the piston is moved, displaced in the case of a linear hydraulic system, pivoted in the case of a rotary hydraulic system, in one direction or another, the pressure level in one of the chambers is increased and the pressure level in the opposite chamber is reduced. In order to make a movement possible at all, there is a fluidic connection between the flexion chamber and the extension chamber. In the fluidic connection, which can be configured as hydraulic channels in the housing or via external lines, a volume exchange of the hydraulic fluid takes place between the chambers. A throttle valve or a control valve can be arranged in the fluidic connections, via which valve the flow resistance from the extension chamber into the flexion chamber and back can be changed. A movement resistance is provided via the setting of the flow resistance, so that, for example when the hydraulic actuator is configured as a damper in a prosthetic joint or orthotic joint, the flexion resistance and/or extension resistance can be changed.

The complex construction of the hydraulic damper with a large number of channels which are arranged in the housing and into which valves must be inserted is a problem.

SUMMARY

The object of the present invention is to provide a solution for a stable hydraulic actuator which can be produced in a simplified manner.

This invention is achieved by a hydraulic actuator and also by a valve block and a screw having the features disclosed herein. Advantageous embodiments and further developments of the invention are given in the description and the figures.

The hydraulic actuator according to the invention having a housing, a chamber which is arranged or formed in the housing and in which a piston is movably mounted and divides the chamber into a flexion chamber and an extension chamber, wherein a channel for hydraulic fluid leads from each of the flexion chamber and the extension chamber into the housing in order to produce a fluidic connection between the flexion chamber and the extension chamber, and at least one valve is arranged in the fluidic connection, provides that the channels lead out of the housing to a valve block in which the at least one valve is arranged and fluidically coupled with the channels, wherein the valve block is connected to the housing.

The channels which are formed or arranged in the housing and which open into the extension chamber or the flexion chamber form part of the fluidic connection in order to allow hydraulic fluid to be conducted from the flexion chamber into the extension chamber and vice versa when the piston moves inside the chamber. The channels lead out of the housing into a valve block in which channels are likewise arranged or formed, wherein the at least one valve is arranged in these flow channels which are arranged or formed in the valve block. By arranging the at least one valve in the valve block, which is connected to the housing, production of the hydraulic actuator is simplified since fewer channels have to be incorporated in the housing wall and in particular smaller channels can be incorporated, since no valves that occupy a larger space than the channels have to be accommodated inside these channels. As a result, the load distribution inside the housing, in particular the housing wall, is equalized, the stresses in the housing are reduced, and it is possible to produce narrower housing walls and narrower housings overall, which can more easily be accommodated in the device in question, for example an orthopedic device in the form of an orthosis, prosthesis or wheelchair. The hydraulic actuator becomes more mechanically robust as a result of the construction, with increased strength as compared with the conventional constructions.

By manufacturing the valve block as a separate component and arranging it on the housing, modular manufacture can be achieved. Moreover, changes at or in the valve block can more easily be implemented. Modifications can more easily be realized, and a modular system can be established in which multiple housing base bodies can be combined with multiple valve blocks in order to be able to assemble different production series.

The valve block is advantageously detachably fixed to the housing in order to facilitate variation and mounting. Moreover, the detachable fixing of the valve block to the housing facilitates maintenance and improves the possibilities of repair.

In a further development of the invention it is provided that at least two control valves and at least two non-return valves are arranged in the valve block in order, within the context of a star architecture of the channels inside the valve block, to be able to influence the flow directions as desired and in addition provide adjustable flow resistances both in the case of extension and in the case of flexion.

A further development of the invention provides that a compensation volume is arranged in the valve block and/or in the housing, which is advantageous in particular when the hydraulic actuator is configured as a linear hydraulic system with a piston and a piston rod. By means of the piston rod, the volume which can be filled with the hydraulic fluid changes according to the position of the piston inside the chamber. In order to be able to hold the excess hydraulic fluid within the hydraulic system when the piston and the piston rod are driven into the chamber, the compensation volume is preferably arranged in the valve block, in order to minimize the housing volume and be able, where possible, to provide inside the valve block all the mechanical systems, adjusting devices and optionally pressure devices for providing a pressure on the hydraulic fluid inside the compensation volume in order that, when the piston rod is moved out of the chamber, the hydraulic fluid is pushed in again. In an embodiment of the invention it is provided that the compensation volume or a further compensation volume is arranged in the housing, for example as part of a chamber.

In an embodiment of the invention, flow channels are arranged in the valve block, all of which flow channels can be fluidically coupled with one another. The fluidic coupling of all the flow channels creates a central point or flow central point at which all the channels that conduct the fluid meet. The meeting point of the flow channels makes it possible to reduce the number of flow channels, since all the valves can be coupled with one another. Moreover, by a suitable arrangement of control valves and non-return valves, all the necessary resistance modifications can be carried out in a simple manner.

A further development of the invention provides that all the flow channels in the valve block are fluidically coupled with a bore. Via the bore, the fluidic connection of all the flow channels is ensured in a simple and reliable manner.

In an embodiment of the invention there is inserted in the bore a screw having connecting channels which connect the flow channels to one another. The connecting channels within the screw preferably connect the flow channels which lead to the channels of the flexion chamber and extension chamber and also to the compensation volume. The valve block can be fixed to the housing via the screw, so that the screw not only produces the mechanical connection of the valve block to the housing but also establishes the hydraulic connection between the extension chamber and the flexion chamber and also the valves and the compensation volume. The screw can be the star point or the meeting point of all the flow channels or can form a meeting point at which all the channels arranged or formed inside the valve block are fluidically coupled with one another. The channels can divide or come together on the path from an inlet into the valve block to an outlet out of the valve block, likewise there can be provided in one or in multiple channels a stop valve which blocks a passage in one flow direction but permits a passage in the other flow direction. Alternatively, the screw can be connected to that meeting point or star point via a flow channel, for example a low-pressure channel. By configuring the screw as a mechanical and hydraulic connection between the housing and the valve block, the overall size both of the valve block and of the housing of the hydraulic actuator can be made smaller, since the complexity of the housing and also of the valve block is reduced.

In the valve block there can be formed a connection for a channel from each of the flexion chamber and the extension chamber, wherein this connection can be configured as a channel or bore which is arranged correspondingly to the respective channel from the flexion chamber or extension chamber when the valve block is mounted on the housing. The connection can divide into two flow channels, of which one is provided with an adjustable throttle valve and the other with a non-return valve. Accordingly, at least four flow channels are arranged inside the valve block, of which in each case two converge to a connection and lead to the channel which leads to the extension chamber or flexion chamber. Accordingly, flow channels branch in pairs from the respective connection, in which flow channels there are arranged servo valves and non-return valves and which lead to the common flow point or star point in which the screw with connecting channels corresponding to the flow channels can be arranged.

A throttle valve is located upstream, in the inflow direction, of the coupling point of the flow channels or the star point at which the flow channels meet, so that the coupling point or the star point is subjected only to hydraulic fluid that has already passed through the throttle valve. It is thereby ensured that, in the case of a throttle valve that is not fully open, only a reduced pressure prevails at the coupling point and flow can take place from the high-pressure side to the low-pressure side.

In order to produce minimal mechanical disturbance in the housing, it is provided in a variant of the invention that exactly two channels lead from the housing, one from the extension chamber and one from the flexion chamber. In principle, the channels can lead out at any desired point of the housing where the valve block can easily be fastened, preferably the valve block is arranged on the end face of the housing, since particularly simple mounting can be achieved here owing to the smooth-faced contact of the valve block with the end face when the piston and the cylinder are round.

The hydraulic actuator is preferably configured as a linear hydraulic actuator with a cylindrical chamber and a piston mounted therein in a longitudinally displaceable manner and a piston rod guided out of the housing.

The invention relates likewise to a valve block for fastening to a hydraulic actuator, wherein at least one valve is arranged in the valve block and can be fluidically coupled with channels from the housing, and the valve block can be connected to the housing.

In a further development of the invention, the valve block is configured as described above.

The invention relates further to a screw having connecting channels which connect together flow channels inside the valve block.

BRIEF DESCRIPTION OF THE DRAWINGS

An exemplary embodiment of the invention will be explained in greater detail hereinbelow with reference to the accompanying figures, in which.

DETAILED DESCRIPTION

Figure 1:
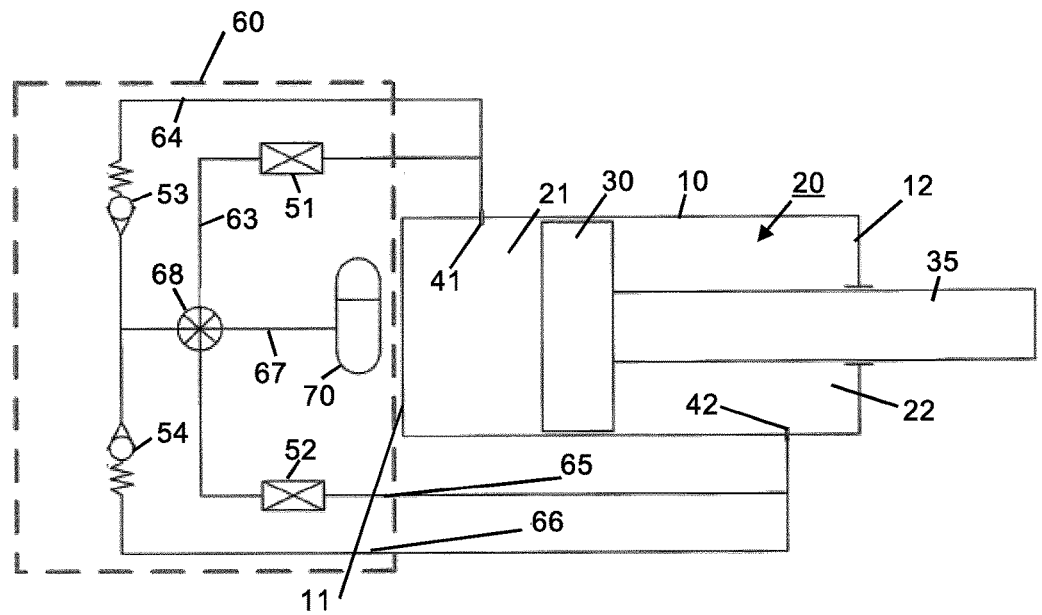
FIG. 1—is a schematic view of a hydraulic actuator in the form of a damper with a mounted valve block.

FIG. 1 shows, in a schematic view, a hydraulic actuator 100 having a housing 10 in which there is formed a cylindrical chamber 20 in which a piston 30 is mounted in longitudinally displaceable manner. The piston 30 is mounted inside the chamber 20 to be displaceable along a longitudinal extent of a piston rod 35 and divides the chamber 20 into a flexion chamber 21 and an extension chamber 22. The piston 30 reduces the volume of the flexion chamber 21 when the piston 30 with the piston rod 35 is driven into the chamber 20. If the piston rod 35 with the piston 30 is moved out of the chamber 20, the volume of the extension chamber 22 is reduced. Extension or flexion occur when the hydraulic actuator 100 is fastened to components which are articulated with one another. If, for example, the piston rod 35 is arranged on an upper part of an orthopedic or prosthetic joint and the housing 10 is arranged on a lower part, for example an upper leg part and a lower leg part, which are then connected together by a prosthetic knee joint or orthotic knee joint, flexion occurs when the piston rod 35 moves inwards and extension occurs when the piston rod moves outwards. The piston 30 is sealed with respect to the inside wall of the chamber 20, so that, when the piston 30 moves inside the chamber 20, hydraulic fluid which is present in the chamber 20 must flow from the flexion chamber 21 into the extension chamber 22 in the case of a flexion movement and from the extension chamber 22 into the flexion chamber 21 in the case of an extension movement. A channel 41, 42 for hydraulic fluid is provided both at the flexion chamber 21 and at the extension chamber 22, through which channel hydraulic fluid from the respective chamber 21, 22 is able to flow in and flow out. The flow direction is dependent on the movement of the piston 30. In the exemplary embodiment shown, exactly one channel 41, 42 leads from the flexion chamber 21 or extension chamber 22 into the housing 10. Fastened to the housing 10 is a valve block 60, which is configured as a separate component. The valve block 60 is shown schematically by the dashed border. Inside the valve block 60 there are formed flow channels 63, 64, 65, 66, 67, which together with the channels 41, 42 form a fluidic connection between the flexion chamber 21 and the extension chamber 22. In the exemplary embodiment according to FIG. 1, two flow channel pairs 63, 64, 65, 66 are formed at the interface between the valve block 60 and the housing 10, which flow channel pairs are positioned corresponding to a channel 41, 42 which is divided into two sections. In the exemplary embodiment according to FIG. 1, the channels 41, 42 of the flexion chamber 21 or extension chamber 22 are divided inside the housing 10 over two channel sections, so that those sections are positioned inside the valve block 60 corresponding to the flow channels 63, 64 or 65, 66 when the valve block is fixed to the housing 10. In the embodiment of the housing 10 that is shown, only exactly one channel 41, 42 leads out of the housing 10 from the flexion chamber 21 or extension chamber 22, so that the housing 10 itself is loaded only with a minimal material loss for forming the respective channel 41, 42. As a result, the stresses inside the housing 10 are reduced, since only a small number of channels 41, 42, namely two, which in addition can be configured to be very short, must be formed.

Inside the valve block 60, the flow channels 63, 64, 65, 66 lead to a bore 68 or a star point at which all the flow channels 63, 64, 65, 66 come together inside the valve block 60 and establish a fluidic connection with one another. Inside the valve block 60 there is also formed a compensation volume 70, which is necessary to compensate for volume fluctuations. The compensation volume 70 is fluidically coupled with the bore 68 or the star point of the flow channels 63, 64, 65, 66, 67 via a flow channel 67.

From the interface of the valve block 60 to the bore 68 or the fluidic star point, control valves 51, 52 and non-return valves 53, 54 are arranged in the separate flow channels 63, 64, 65, 66. From the flexion chamber 21, a first flow channel 63 leads via a first control valve 51 to the common bore 68, as does a second flow channel 64 which is equipped with a first spring-loaded non-return valve 53. The first non-return valve 53 blocks a fluid passage from the flexion chamber 21 in the direction towards the common bore 68 and also to the extension chamber 22. Accordingly, in the event of flexion or when the piston 30 is driven into the chamber 20 in order to reduce the volume within the flexion chamber 21, the whole of the hydraulic fluid must pass through the first control valve 51 before it is conducted via the common bore 68 or the star point to the compensation volume 70 or to the control valves 52, 54 which are arranged as a mirror image. The second control valve 52 and the second non-return valve 54 are connected via flow channels 65, 66 to the channel 42 which leads to the extension chamber 22. From the common bore 68 or the fluidic star point 68, a flow channel leads via the second control valve 52 to the extension chamber 22 and a further flow channel 66, in which the second spring-loaded non-return valve 54 is arranged, leads to the extension chamber 22 or the channels inside the housing 10 which lead to the channel 42 to the extension chamber 22. The two non-return valves 53, 54 are coupled with one another and with the common bore 68 via a connecting channel. Alternatively, the flow channels 64, 66 inside the valve block 60 that are associated with the non-return valves 53, 54 are conducted separately to the common bore 68 or the fluidic star point. The non-return valves 53, 54 block a high-pressure line to the common hydraulic star point 68 and permit a flow into a low-pressure chamber from the star point 68 only once a control valve 51, 52 on the high pressure side has been passed.

The common bore 68 does not have to be a cylindrical bore; the important factor is that a point or a fluidic space is formed at which all the low-pressure lines meet.

High-pressure lines are the lines or flow channels into which hydraulic fluid is pushed directly from the respective chamber; low-pressure lines are those channels that are located after a control valve 51, 52 or a non-return valve 53, 54, when seen in the flow direction, and lead either to the star point 68, the compensation volume 70 or to the particular low-pressure chamber into which the hydraulic fluid flows.

Figure 2:
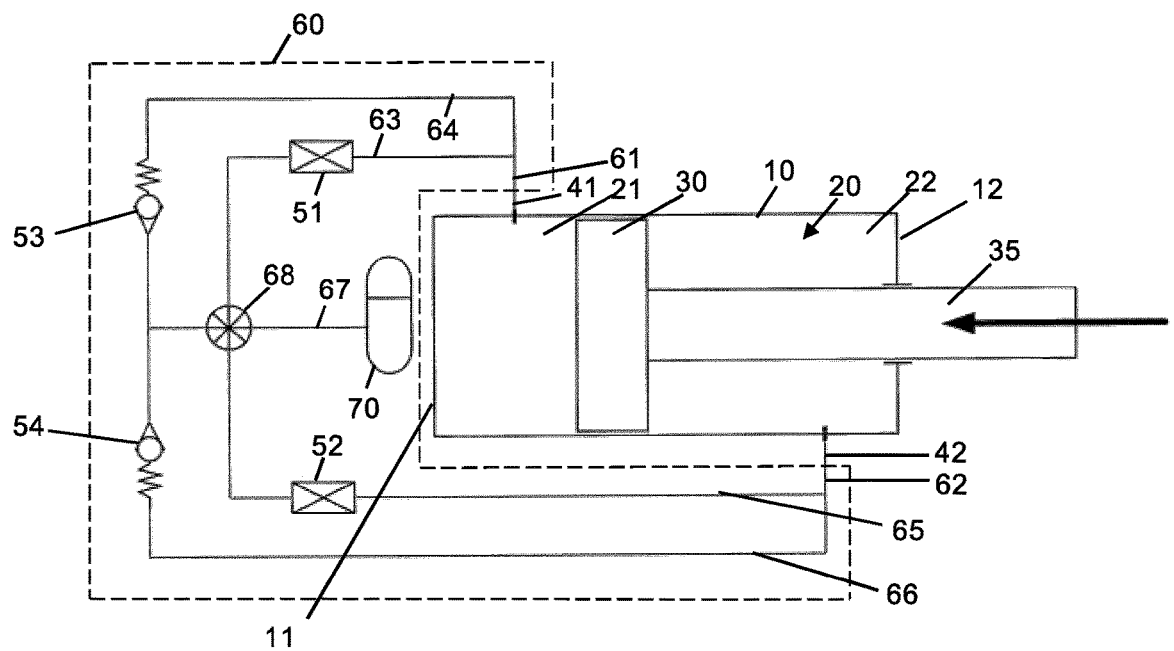
FIG. 2—is a schematic view of a variant of the invention in the case of a flexion movement.

FIG. 2 shows a variant of the invention in which the valve block 60 is coupled with the housing 10 only via two channel interfaces. In a mounted state, a first channel 41 is positioned opposite a first connection 61 and so arranged, and a second channel 42 is positioned opposite a second connection 62 and so arranged, that hydraulic fluid is able to flow from the flexion chamber 21 into the extension chamber 22. In the exemplary embodiment shown, the channels 41, 42 extend radially outwards out of the housing 10. Alternatively, it is possible and provided that the channels 41, 42 are guided out at an end face 11, 12 of the housing 10 and run at least partially parallel to the direction of movement of the piston 30. The valve block 60 is then screwed to the housing 10 or fixed thereon at the end face. If, alternatively, the valve block 60 is fastened to the housing 10 at the side, this reduces the overall length of the hydraulic actuator, so that such a variant is chosen when little installation space is available. Inside the valve block 60, the respective connection 61, 62 divides into two flow channels 63, 64, 65, 66. The piston 30 is moved to the left in the direction indicated by the arrow via the piston rod 35, so that the flexion chamber 21 becomes smaller and the hydraulic fluid in the flexion chamber 21 is placed under pressure. The hydraulic fluid flows out of the flexion chamber 21 through the channel 41 into the connection 61 and, from there, into the two flow channels 63, 64. Owing to the first stop valve 53, no hydraulic fluid will pass through the upper flow channel 64. The hydraulic fluid is therefore conducted through the first control valve 51 in the direction towards the bore 68 or the common flow star point. From the bore 68, the hydraulic fluid, throttled after passing through the first control valve 51, passes, depending on the valve position, either through the control valve 52, through the non-return valve 54 or through the second control valve 52 and also through the second non-return valve 54. After passing through the respective valve 52, 54, the hydraulic fluid is conducted through the channels 65, 66 to the connection 62 and, from there, through the channel 42 into the extension chamber 22. Since in the case of the flexion movement, that is to say when the piston 30 is displaced to the left, the piston rod 35 enters the extension chamber 22, the available chamber volume is reduced by the volume of the entering piston rod 35, so that a portion of the hydraulic fluid from the flexion chamber 21 flows through the flow channel 67 into the compensation volume 70. The damping resistance in the flexion direction can be adjusted via the first control valve 51 as well as via the spring loading of the second non-return valve 54 and also the second control valve 52.

Figure 3:
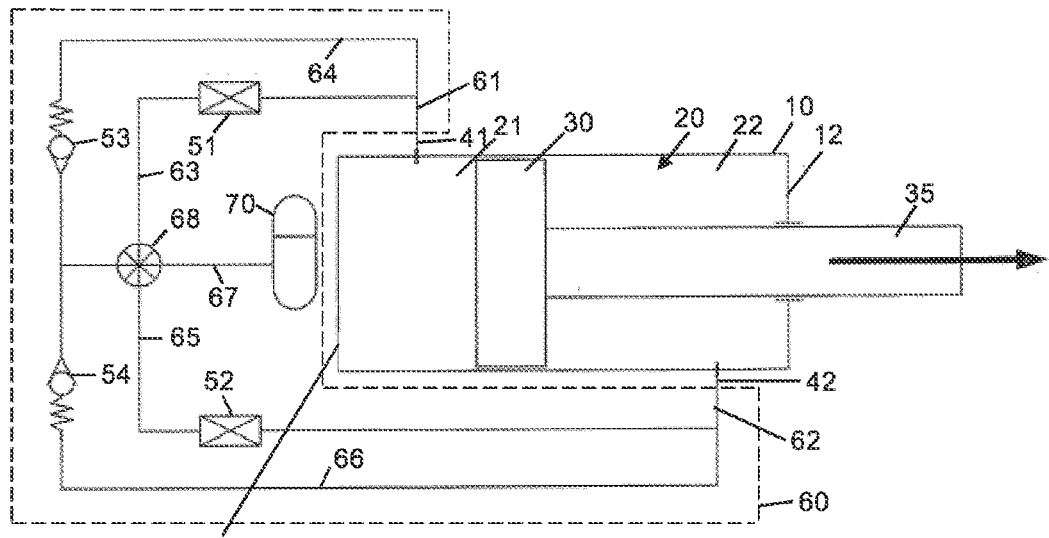
FIG. 3—shows an embodiment of the invention in the case of an extension movement.

In the case of an opposite movement, which is shown in FIG. 3, the piston rod 35 is pulled out of the extension chamber 22, the piston 30 is moved to the right. Accordingly, a force is exerted on the hydraulic fluid inside the extension chamber 22, and the hydraulic fluid under pressure passes through the channel 42 into the connection 62 and, from there, into the flow channels 65 and 66. The second non-return valve 54 blocks the passage through the flow channel 66, so that the hydraulic fluid flows out of the extension chamber 22 through the second control valve 52 and the flow channel 65 to the bore 68. From there, it passes through the first non-return valve 53 and the first control valve 51, through the channels 63, 64, to the first connection 61 and into the flexion chamber 21. The volume of hydraulic fluid that is lacking is provided from the compensation volume 70 under pressure.

Figure 4:
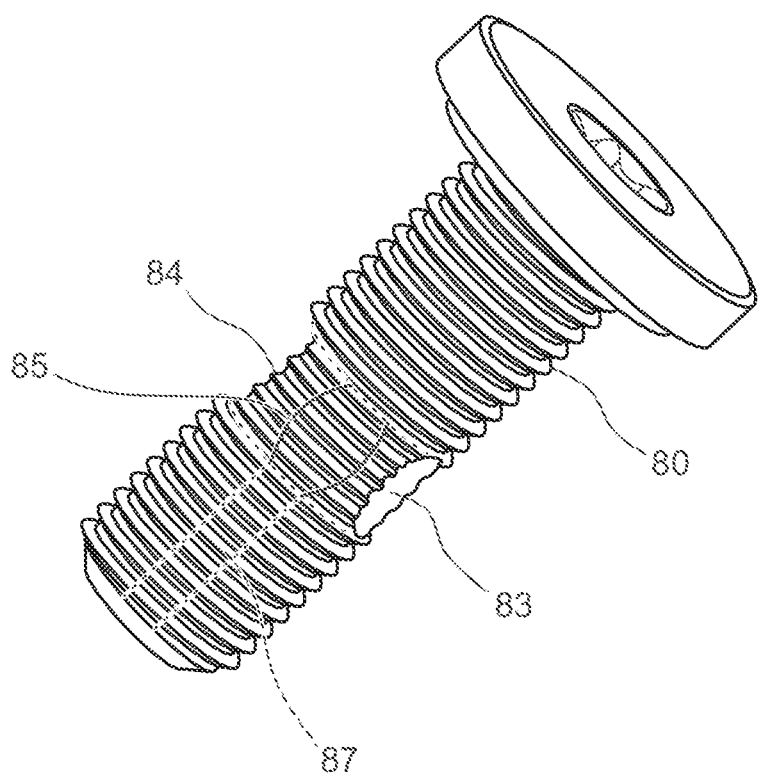
FIG. 4—is a perspective view of a connecting screw.

FIG. 4 shows a possible configuration of the bore 68 or of the fluidic star point in the form of a screw 80, in which four connecting channels for connecting the flow channels 63, 64, 65, 66, 67 are formed. The connecting channels 83, 84, 85 are visible, the fourth connecting channel, which connects the flow channel 66 from the second non-return valve 54 to the remaining flow channels 63, 64, 65, 67, is not shown. It is likewise possible to provide only three connecting channels 83, 84, 85 if the flow channels 66, 64 downstream of the non-return valves 53, 54 are combined to form a common channel. A T-shaped crossing of the connecting channels 83, 84, 85 is obtained. The connecting channels are formed radially with respect to the longitudinal extent of the screw shaft. In the exemplary embodiment shown, the connecting channels 83, 84, 85 meet in the middle inside the screw shaft. In addition, a connecting channel 87 formed in the longitudinal extent of the screw shaft leads to the compensation volume 70, or to the flow channel 67 which leads to the compensation volume 70. Accordingly, by means of the screw 80, on the one hand a fluidic connection between all the flow channels 63, 64, 65, 66, 67 and on the other hand a mechanical connection between the valve block 60 and the housing 10 are formed. The screw 80 forms the connection of at least two low-pressure channels and can at the same time provide a mechanical connection of multiple components of a linear hydraulic system. The screw 80 does not necessarily have to be the fluidic star point or connecting point but may also be connected via a low-pressure channel to the star point or the bore 68.

By a combination of mechanical fixing of the valve block 60 at or in the housing 10 and a fluidic connection of all the channels in the screw 80, the overall size of the hydraulic actuator is made smaller. Moreover, the complexity of the cylinder with the housing 10 and the piston 30 located therein is greatly reduced. Only two channels 41, 42 lead out of the housing 10 and conduct the hydraulic fluid into the valve block 60, in which the control valves 51, 52, the non-return valves 53, 54 and the compensation volume 70 are arranged.

Figure 5:
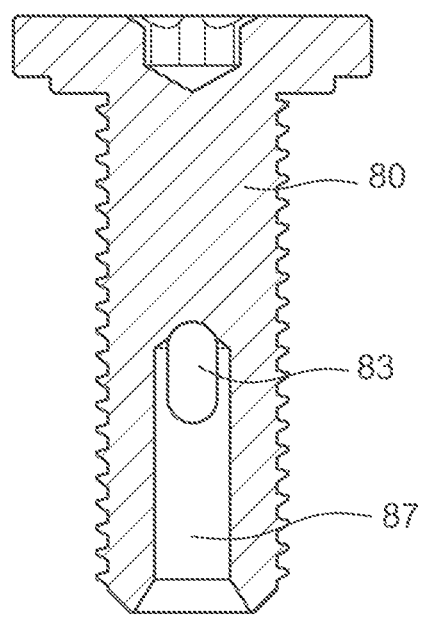
FIG. 5—is a sectional view of the connecting screw according to FIG. 4.

FIG. 5 shows the screw 80 in a sectional view. The configuration of the connecting channel 87 in the longitudinal extent of the screw shaft and the perpendicular orientation of a connecting channel 83, which is oriented radially with respect to the longitudinal extent of the screw 80, are shown.

Figure 6:
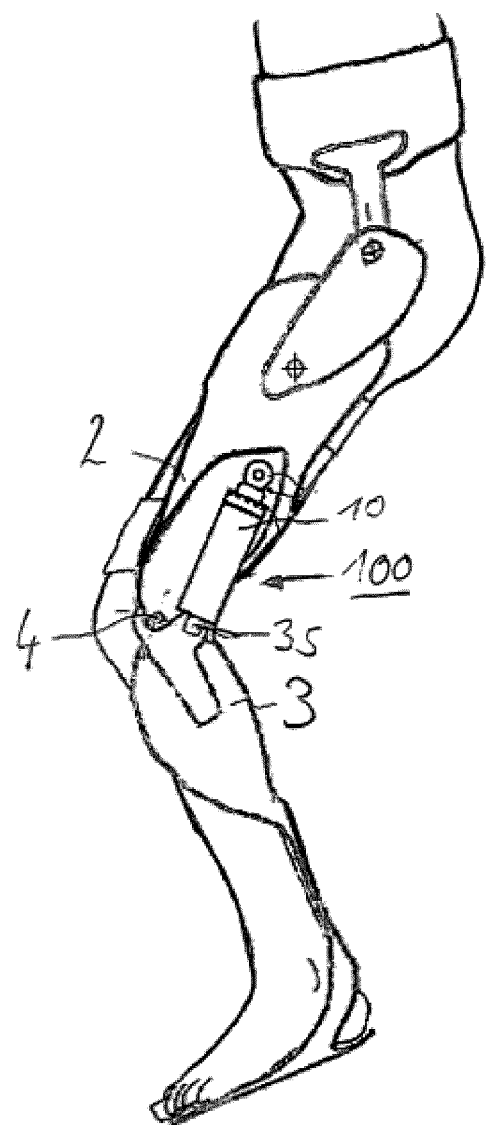
FIG. 6—shows an application example in an orthosis.

FIG. 6 shows an application example of a connection of a hydraulic actuator 100 to an orthosis. In the exemplary embodiment shown, the orthosis bridges all the joints of the lower limb. The hydraulic actuator 100 is fastened at a distal fastening point to an upper leg part 2, which is fastened to an upper leg via fastening straps. The upper leg part 2 is connected proximally in an articulated manner to a waist strap or a hip socket and distally in an articulated manner via a pivot axis 4 to a lower leg part 3, which has a foot support. The lower part 3 can be pivoted about the pivot axis 4 relative to the upper leg part 2 in the extension direction and flexion direction. The hydraulic actuator 100 is mounted both on the upper leg part 2 and on the lower leg part 3. The piston rod 35, which protrudes from the housing 10, is fastened to the lower leg part 3. Pivot movements between the upper leg part 2 and the lower leg part 3 are assisted or damped by the hydraulic actuator 100.

Figure 7:
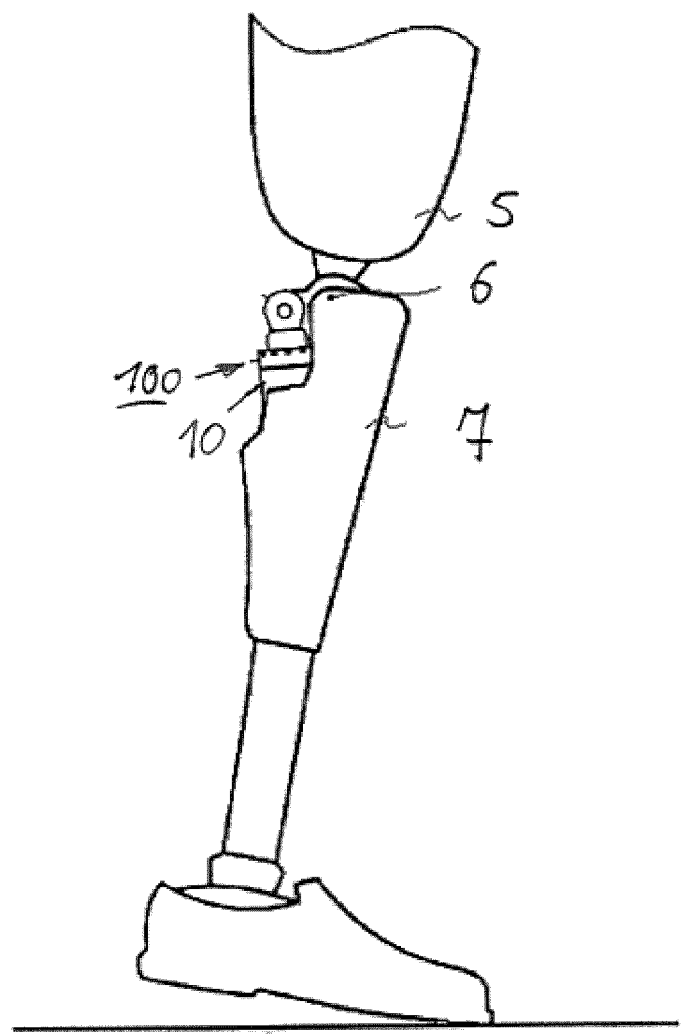
FIG. 7—shows an application example in a prosthesis.

An alternative application example is shown in FIG. 7, in which the hydraulic actuator 100 is arranged between a prosthesis upper part 5 in the form of an upper leg socket and a lower leg part 7. The upper part 5 and the lower part 7 are connected to one another in a prosthetic knee joint to be pivotable about a pivot axis 6. The housing 10 with a bearing seat is fastened to the upper part 5 on an arm, while the piston rod, which is not visible, is mounted on the lower leg part 7. On flexion and on extension, the hydraulic actuator 100 is subjected to linear forces and the piston rod is driven into or pulled out of the housing 10.

We claim:

1. A hydraulic actuator comprising:
   a housing;
   a chamber which is arranged or formed in the housing;
   a piston is movably mounted in and dividing the chamber into a flexion chamber and an extension chamber;
   a plurality of channels for hydraulic fluid, the channels leading from each of the flexion chamber and the extension chamber into the housing in order to produce a fluidic connection between the flexion chamber and the extension chamber;
   a valve arranged in the fluidic connection;
   a valve block in which the valve is arranged and fluidically coupled with the channels, the valve block being fastened to the housing, and the channels leads out of the housing to the valve block, the valve block comprises a plurality of channels, wherein all the channels in the valve block are fluidically coupled with a bore; and
   a screw having connecting channels which connect the channels to one another, the screw being inserted in the bore.

2. The hydraulic actuator as claimed in claim 1, wherein the valve block is detachably fastened to the housing.

3. The hydraulic actuator as claimed in claim 1, wherein the valve comprises a plurality of valves comprising at least two control valves and at least two non-return valves arranged in the valve block.

4. The hydraulic actuator as claimed in claim 1, further comprising a compensation volume arranged in the valve block or in the housing.

5. The hydraulic actuator as claimed in claim 1, wherein the screw fixes the valve block to the housing.

6. The hydraulic actuator as claimed in claim 1, further comprising a plurality of connections for the channels from the flexion chamber and the extension chamber are formed in the valve block and the connections are each connect to two of the passages, of which one is provided with an adjustable throttle valve and the other with a non-return valve.

7. The hydraulic actuator as claimed in claim 1, wherein a throttle valve is located upstream, in an inflow direction, of the bore.

8. The hydraulic actuator as claimed in claim 1, wherein the channels include exactly two channels that lead out of the housing.

9. The hydraulic actuator as claimed in claim 1, wherein the valve block is arranged on an end face of the housing.

10. The hydraulic actuator as claimed in claim 1, wherein the hydraulic actuator is configured as a linear hydraulic actuator, wherein the chamber comprises a cylindrical chamber, the piston is longitudinally displaceable within the cylindrical chamber, and wherein the hydraulic actuator further comprises a piston rod attached to the piston and extending out of the housing.

11. A hydraulic actuator comprising:
a housing;
a chamber arranged or formed in the housing;
a piston movably mounted in the chamber, the piston dividing the chamber into a flexion chamber and an extension chamber;
a plurality of channels providing fluid communication between the flexion chamber and the extension chamber, the channels carrying hydraulic fluid;
a valve block in which a valve is arranged and fluidically coupled with the channels, the valve block being connected to the housing, the channels leading out of the housing to the valve block, the valve block comprises a plurality of channels, wherein all the channels in the valve block are fluidically coupled with a bore, wherein the valve is arranged in one of the channels of the valve block; and
a screw having connecting channels which connect the channels to one another, the screw being inserted in the bore.

12. The hydraulic actuator as claimed in claim 11, wherein the valve block is detachably fastened to the housing.

13. The hydraulic actuator as claimed in claim 11, wherein the valve comprises a plurality of valves comprising at least two control valves and at least two non-return valves arranged in the valve block.

14. The hydraulic actuator as claimed in claim 11, further comprising a compensation volume arranged in the valve block or in the housing.

* * * * *